US010960051B2

(12) United States Patent
Yang et al.

(10) Patent No.: US 10,960,051 B2
(45) Date of Patent: Mar. 30, 2021

(54) METHODS OF TREATING DRY EYE SYNDROME

(71) Applicant: REGENTREE, LLC, Princeton, NJ (US)

(72) Inventors: Won Suk Yang, Princeton, NJ (US); Sin Wook Kang, Gyeonggi-do (KR); Kyoungsun Kim, Busan (KR)

(73) Assignee: REGENTREE, LLC, Princeton, NJ (US)

( * ) Notice: Subject to any disclaimer, the term of this patent is extended or adjusted under 35 U.S.C. 154(b) by 0 days.

(21) Appl. No.: 16/318,571

(22) PCT Filed: Jul. 17, 2017

(86) PCT No.: PCT/US2017/042382
§ 371 (c)(1),
(2) Date: Jan. 17, 2019

(87) PCT Pub. No.: WO2018/017479
PCT Pub. Date: Jan. 25, 2018

(65) Prior Publication Data
US 2019/0240294 A1    Aug. 8, 2019

Related U.S. Application Data

(60) Provisional application No. 62/363,565, filed on Jul. 18, 2016, provisional application No. 62/363,592, filed on Jul. 18, 2016, provisional application No. 62/436,727, filed on Dec. 20, 2016.

(51) Int. Cl.
| *A61K 38/04* | (2006.01) |
| *A61K 47/02* | (2006.01) |
| *A61K 9/06* | (2006.01) |
| *A61K 9/08* | (2006.01) |
| *A61K 38/16* | (2006.01) |
| *A61P 27/02* | (2006.01) |
| *A61K 38/22* | (2006.01) |
| *A61K 9/00* | (2006.01) |

(52) U.S. Cl.
CPC ........ *A61K 38/2292* (2013.01); *A61K 9/0048* (2013.01); *A61K 9/06* (2013.01); *A61K 9/08* (2013.01); *A61K 38/04* (2013.01); *A61K 47/02* (2013.01); *A61P 27/02* (2018.01)

(58) Field of Classification Search
CPC .... A61K 38/04; A61K 38/2292; A61K 47/02; A61K 9/0048; A61K 9/06; A61K 9/08; A61K 38/16; A61P 27/02
USPC .......................................... 514/20.8, 1.1, 12
See application file for complete search history.

(56) References Cited

U.S. PATENT DOCUMENTS

| 2004/0131626 | A1* | 7/2004 | Goldstein | .............. A61K 38/08 424/184.1 |
| 2008/0096817 | A1* | 4/2008 | Goldstein | .......... A61K 38/2292 514/12.9 |
| 2012/0071411 | A1* | 3/2012 | Crockford | ............ A61K 9/0048 514/12.9 |
| 2013/0303557 | A1 | 11/2013 | Beals et al. | |

FOREIGN PATENT DOCUMENTS

| WO | WO 91/12808 | 9/1991 |
| WO | WO 02/074193 | 9/2002 |

OTHER PUBLICATIONS

Huff et al., "Beta-Thymosin, small acidic peptides with multiple functions," The International Journal of Biochemistry & Cell Biology, 33: 205-220. (Year: 2001).*
Hannappel et al., "Actin-sequestering ability of thymosin beta 4, thymosin beta 4 fragments, and thymosin beta 4-like peptides as assessed by the DNase I inhibition assay," Biol. Chem. Hoppe Seyler, 374(2); 117-122. Only abstract enclosed. (Year: 1993).*
Thymosin Beta 4 sequence from www.prospecbio.com/thymosin_beta-4, pp. 1-6. (Year: 2020).*
2007 Report of the International Dry Eye WorkShop (DEWS), The Ocular Surface, 5(2):59 pages (2007).
Hannappel et al., "Determination of Thymosin $\beta_4$ in Human Blood Cells and Serum," Journal of Chromatography, 397:279-285 (1987).
Huff et al., "Thymosin $\beta^4$ is Released from Human Blood Platelets and Attached by Factor XIIIa (Transglutaminase) to Fibrin and Collagen," The FASEB Journal, 16:691-696 (2002).
International Search Report and Written Opinion dated Sep. 26, 2017 in International Application No. PCT/US2017/042382.
Ruff et al., A Randomized, Placebo-Controlled, Single and Multiple Dose Study of Intravenous Thymosin $\beta_4$ in Healthy Volunteers, Annals of the New York Academy of Sciences, 1194:223-229 (2010).
Sosne et al., "Biological Activities of Thymosin $\beta_4$ Defined by Active Sites in Short Peptide Sequences," The FASEB Journal, 24:1-8 (2010).
Sosne et al., "Thymosin Beta 4 Ophthalmic Solution for Dry Eye: A Randomized, Placebo-Controlled, Phase II Clinical Trial Conducted Using the Controlled Adverse Environment (CAE™) Model," Clinical Ophthalmology, 9:877-884 (2015).
Sosne et al., "Thymosin $\beta_4$ Significantly Reduces the Signs of Dryness in a Murine Controlled Adverse Environment Model of Experimental Dry Eye", Expert Opinion on Biological Therapy, 15(Suppl.1):155-161 (2015).

(Continued)

*Primary Examiner* — Julie Ha
(74) *Attorney, Agent, or Firm* — Baker Botts L.L.P.

(57) ABSTRACT

Methods of treating dry eye syndrome (DES) with an effective amount of thymosin beta 4 (Tβ4), Tβ4 fragments, Tβ4 isoforms, Tβ4 derivatives, peptide agents including amino acid sequence LKKTET [SEQ ID NO: 1] or LKKTNT [SEQ ID NO:2], or variants thereof are provided. The presently disclosed subject matter provides methods of increasing tear volume, increasing tear film stability, decreasing ocular surface damage, and decreasing ocular discomfort by delivering compositions of thymosin beta 4 or fragments thereof to subjects in need.

8 Claims, 4 Drawing Sheets

Specification includes a Sequence Listing.

(56) References Cited

OTHER PUBLICATIONS

Sosne et al., "Thymosin $\beta_4$ Promotes Human Conjunctival Epithelial Cell Migration," Current Eye Research, 24(4):268-273 (2002).
Supplementary European Search Report dated Nov. 28, 2019 in European Application No. 17831632.9.
Zeev et al. "Diagnosis of Dry Eye Disease and Emerging Technologies", Clinical Ophthalmology, 8:581-590 (2014).

* cited by examiner

SEQUENCE LISTING

```
<160> NUMBER OF SEQ ID NOS: 2

<210> SEQ ID NO 1
<211> LENGTH: 6
<212> TYPE: PRT
<213> ORGANISM: Homo sapiens

<400> SEQUENCE: 1

Leu Lys Lys Thr Glu Thr
1               5

<210> SEQ ID NO 2
<211> LENGTH: 6
<212> TYPE: PRT
<213> ORGANISM: Homo sapiens

<400> SEQUENCE: 2

Leu Lys Lys Thr Asn Thr
1               5
```

METHODS OF TREATING DRY EYE SYNDROME

CROSS-REFERENCE TO RELATED APPLICATIONS

This application is a U.S. National Stage Patent Application under 35 U.S.C. § 371 of International Application No. PCT/US2017/042382, filed on Jul. 17, 2017, which claims priority under 35 U.S.C. § 119 to U.S. Application Ser. No. 62/363,565, filed Jul. 18, 2016, U.S. Application Ser. No. 62/363,592, filed Jul. 18, 2016, and U.S. Application Ser. No. 62/436,727, filed Dec. 20, 2016, all of which are hereby incorporated by reference herein in their entireties.

FIELD OF THE INVENTION

The presently disclosed subject matter relates to methods for treating or preventing dry eye syndrome and the symptoms associated with the same. Specifically, the presently disclosed subject matter relates to methods of increasing tear amounts, increasing tear film stability, decreasing ocular discomfort, and reducing ocular surface damage.

SEQUENCE LISTING

The specification further incorporates by reference the Sequence Listing submitted herewith via EFS on Jul. 17, 2017. Pursuant to 37 C.F.R. § 1.52(e)(5), the Sequence Listing text file, identified as 085089_0102seqlisting, is 554 bytes and was created on Jul. 17, 2017. The Sequence Listing, electronically filed herewith, does not extend beyond the scope of the specification and thus does not contain new matter.

BACKGROUND OF THE INVENTION

Dry eye syndrome (DES) is a common eye disorder affecting an estimated 25 to 30 million people in the United States, with prevalence estimates varying widely from 7.8% to almost 58%.

Incidence of DES rises sharply with age, with women being affected more than men, purportedly due to the pathophysiological role of androgens and the complex nexus of the endocrine-immunological systems. The Dry Eye WorkShop (DEWS), established by the Tear Film & Ocular Surface Society (TFOS), has redefined dry eye as "a multifactorial disease of the tears and ocular surface that results in symptoms of discomfort, visual disturbance, and tear film instability with potential damage to the ocular surface, accompanied by increased osmolality of the tear film and inflammation of the ocular surface." See "The definition and classification of dry eye disease", Report of the Definition and Classification Subcommittee of the International Dry Eye WorkShop (2007).

Approaches to treatment have varied in the past. However, disease modification has generally targeted the inflammatory aspects of the disease. In fact, currently approved therapies for dry eye disease are the use of cyclosporine ophthalmic emulsion (Restasis®) or lifitegrast ophthalmic solution (Xiidra®), which target the inflammation response of the disease. A focus on treatments that could reduce the inflammatory responses while accelerating corneal epithelial healing would represent a major step forward from current treatment options. The presently disclosed subject matter addresses this need with thymosin beta 4 (Tβ4), a naturally-occurring polypeptide, which has been found to elicit a spectrum of therapeutic responses, including but not limited to, rapid corneal re-epithelialization and reduction in corneal inflammation.

Thymosin beta 4 (Tβ4) is a low molecular weight, 43-amino acid protein that is critical to cell survival due to its unique, broad-ranging wound healing and anti-inflammatory activities that are active at different stages of tissue repair. See Sosne et al., FASEB J. 2010; 24: 2144-51. Tβ4 is present in high concentrations (up to about 0.4 to 2.1 µg/ml in human serum) in all tissue types except red blood cells, with highest levels occurring in platelets, white blood cells, plasma and wound fluid. See Hannappel & van Kampen, 1987 J Chromatography, 397:279-85; Huff et al., 2001 FASEB J 16:691-6; and Sosne et al., 2002 Cur. Eye Res. 24: 268-273.

In a Phase I clinical trial, an injectable solution of Tβ4 for promoting cell survival during cardiac ischemia was administered for 14 consecutive days at four escalating dose levels. The administration was deemed safe and well-tolerated. See Ruff et al., 2010 Ann N.Y. Acad. Sci. 1194:223-229. In another Phase I clinical trial, a total of 20 healthy patients (i.e., without DES) were given a single intravenous dose of Tβ4 for assessing safety of the Tβ4 composition. See Ruff et al., 2010 Ann N.Y. Acad. Sci. 1194:223-229.

In a Phase II clinical trial, the safety and efficacy of a Tβ4 ophthalmic formulation was evaluated in patients with DES using the Controlled Adverse Environment (CAE®, Ora, Inc.) model. See Sosne et al., 2015 Clin Ophthal 9:877-884. A total of 72 subjects were given either 0.1% Tβ4 or placebo treatment for a total of 28 days. The primary efficacy end points were measured on day 29. Secondary end points were measured over the course of the study. Despite a lack of adverse events reported, the primary endpoints did not show a significant difference between treatment and control groups on day 29. Although some differences between treatment groups were observed for secondary endpoints, these efficacy endpoints were assessed with one treatment regimen. Thus, optimization of a treatment regimen and high degree of individual patient variability are desired to confirm and extend therapeutic effects of the disclosed effects of the Tβ4 ophthalmic formulation.

Accordingly, there is an ongoing need for new methods for the treatment of DES. Described herein are methods for such effective treatments of DES.

SUMMARY OF THE INVENTION

The present disclosure provides ophthalmic compositions and methods for treating dry eye syndrome. The method can include delivering a composition containing thymosin beta 4 (Tβ4), Tβ4 fragments, Tβ4 isoforms, Tβ4 derivatives, peptide agents including amino acid sequence LKKTET [SEQ ID NO:1] or LKKTNT [SEQ ID NO:2], or variants thereof to an affected eye of a subject.

In certain aspects, the present disclosure provides a method of increasing tear amounts in a subject in need thereof, wherein the method comprises delivering a composition containing Tβ4, Tβ4 fragments, Tβ4 isoforms, Tβ4 derivatives, peptide agents including amino acid sequence LKKTET [SEQ ID NO:1] or LKKTNT [SEQ ID NO:2], or variants thereof to an affected eye of the subject. In particular embodiments, the subject can have DES characterized by a tear volume test score of less than about 10 mm in the affected eye.

In certain aspects, the present disclosure provides a method of increasing tear film stability in a subject in need thereof, wherein the method comprises delivering a composition containing Tβ4, Tβ4 fragments, Tβ4 isoforms, Tβ4 derivatives, peptide agents including amino acid sequence LKKTET [SEQ ID NO:1] or LKKTNT [SEQ ID NO:2], or variants thereof to an affected eye of the subject. In particular embodiments, the subject can have DES characterized by a tear film break up time of less than about 10 seconds in the affected eye.

In certain aspects, the present disclosure provides a method of decreasing ocular surface damage in a subject in need thereof, wherein the method comprises delivering a composition containing Tβ4, Tβ4 fragments, Tβ4 isoforms, Tβ4 derivatives, peptide agents including amino acid sequence LKKTET [SEQ ID NO:1] or LKKTNT [SEQ ID NO:2], or variants thereof to an affected eye of the subject. In particular embodiments, the subject can have DES characterized by a fluorescein staining score of about 4 or higher in the affected eye. Further, in particular embodiments, the subject can have DES characterized by a tear film break up time of less than about 10 seconds in the affected eye.

In certain aspects, the present disclosure provides a method of decreasing ocular discomfort in a subject in need thereof, wherein the method comprises delivering a composition containing Tβ4, Tβ4 fragments, Tβ4 isoforms, Tβ4 derivatives, peptide agents including amino acid sequence LKKTET [SEQ ID NO:1] or LKKTNT [SEQ ID NO:2], or variants thereof to an affected eye of the subject. In particular, the subject has DES characterized by an ocular discomfort score of about 2 or higher in the affected eye.

In certain aspects, the present disclosure provides a method of treating DES in a subject in need thereof, wherein the method comprises delivering a composition containing Tβ4, Tβ4 fragments, Tβ4 isoforms, Tβ4 derivatives, peptide agents including amino acid sequence LKKTET [SEQ ID NO:1] or LKKTNT [SEQ ID NO:2], or variants thereof to an affected eye of the subject. The DES can be characterized by decreased tear amount, decreased tear film stability, increased ocular surface damage, increased ocular discomfort, or combinations thereof.

In certain embodiments, the composition comprises from about 0.05% to about 0.1% by weight Tβ4, Tβ4 fragments, Tβ4 isoforms, Tβ4 derivatives, peptide agents including amino acid sequence LKKTET [SEQ ID NO:1] or LKKTNT [SEQ ID NO:2], or variants thereof. As embodied herein, the composition can be formulated as a solution. For example, and not limitation, the solution including Tβ4, Tβ4 fragments, Tβ4 isoforms, Tβ4 derivatives, peptide agents including amino acid sequence LKKTET [SEQ ID NO:1] or LKKTNT [SEQ ID NO:2], or variants thereof can be delivered to the subject in a form of eye drops. In certain embodiments, the composition can be used in combination with artificial tears.

In certain embodiments, the method can further include delivering artificial tears to the affected eye of the subject. For example, and not limitation, the artificial tears can be delivered simultaneously with the composition. In some embodiments, the artificial tears and the composition can be delivered sequentially.

In certain embodiments, the composition can be delivered to the subject at least once per day but no more than four times per day. For example, and not limitation, the composition can be delivered to the subject once, twice, three, or four times per day.

In certain embodiments, the present disclosure provides an ophthalmic composition comprising an effective amount of Tβ4, Tβ4 fragments, Tβ4 isoforms, Tβ4 derivatives, peptide agents including amino acid sequence LKKTET [SEQ ID NO:1] or LKKTNT [SEQ ID NO:2], or variants thereof, wherein the composition is effective in treating DES in a subject in need thereof.

Other features and advantages of the disclosure will be apparent from the following detailed description, figures, and claims.

DETAILED DESCRIPTION OF THE DISCLOSURE

Figure 1:
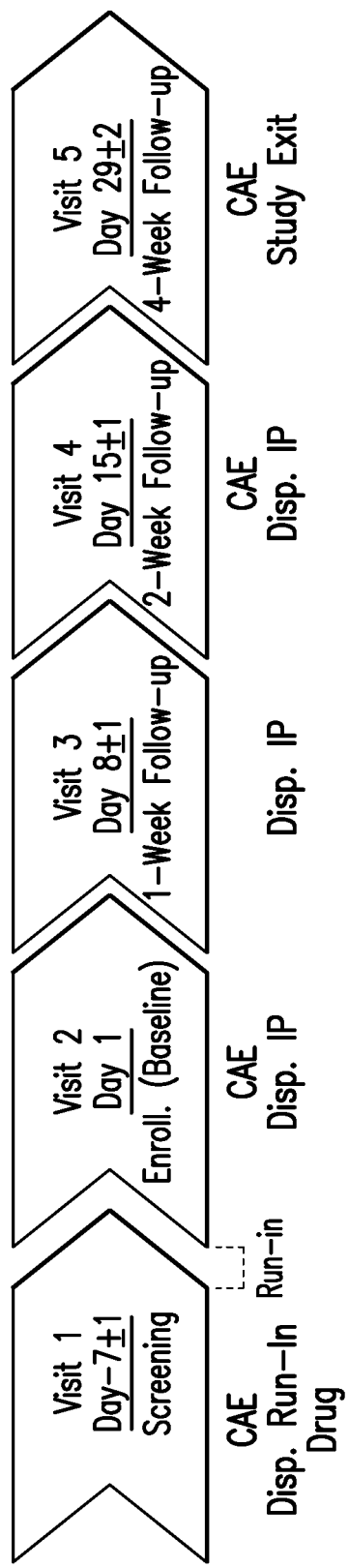
FIG. 1 provides a flow chart depicting a study design to evaluate the efficacy and safety of a 0.05% Tβ4 ophthalmic composition and a 0.1% Tβ4 ophthalmic composition compared to a placebo composition.

Provided herein, inter alia, is a method of treating ophthalmic diseases (e.g., DES) in a subject in need thereof, wherein the method is directed to the use of an ophthalmic composition that contains human Tβ4 or fragments thereof. These and other aspects of the presently disclosed subject matter are discussed more in the detailed description and examples.

Definitions

Unless defined otherwise, all technical and scientific terms used herein have the meaning commonly understood by a person skilled in the art to which this disclosure belongs. The following references provide one of skill with a general definition of many of the terms used in this disclosure: The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). Certain terms are defined below to provide additional guidance in describing the compositions and methods of the disclosed subject matter and how to use them.

As used herein, the following terms have the meanings ascribed to them below, unless specified otherwise. Abbreviations used herein have their conventional meaning within the chemical and biological arts.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about. About with respect to concentration range of the compositions of the current disclosure also refers to any variation of a stated amount or range which would be an effective amount or range.

As used herein, "additive" can include any additional components that can be added to the composition as described herein. One or more additives can be added to the composition. Exemplary additives can include preservatives, viscosity agents, buffering agents, hypertonic agents, isotonic agents, and pH adjustment agents. Additives in the current disclosure can be used in any suitable amount.

As used herein, the term "administering" can mean any suitable route, i.e., via oral administration, via topical administration (e.g., eye drops or a spray), or intraocular administration.

As used herein, the term "co-administer" is meant that a composition described herein is administered at the same time, just prior to, or just after the administration of additional therapies. The composition of the disclosure can be administered alone or can be co-administered with a second composition/therapeutic agent to a subject. Co-administration is meant to include simultaneous or sequential administration of the composition individually or in combination with a second composition/therapeutic agent. Additionally, the first and second agents can be formulated separately or together in one or more compositions.

As used herein, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

As used herein, "concurrent administration" includes overlapping in duration at least in part. For example, when two agents (e.g., any of the compositions described herein) are administered concurrently, their administration occurs within a certain desired time. The compositions' administration can begin and end on the same day. The administration of one composition can also precede the administration of a second composition by day(s) as long as both compositions are taken on the same day at least once. Similarly, the administration of one composition can extend beyond the administration of a second composition as long as both compositions are taken on the same day at least once. The compositions do not have to be taken at the same time each day to include concurrent administration.

As used herein, "conservative variant" or grammatical variations thereof can denote the replacement of an amino acid residue by another biologically similar residue. Examples of conservative variations include the replacement of a hydrophobic residue, such as isoleucine, valine, leucine or methionine for another, the replacement of a polar residue for another, such as the substitution of arginine for lysine, glutamic for aspartic acids, or glutamine for asparagine, and the like.

As used herein, the term, "CAE" refers to a clinical model that provides a standardized approach to studying investigational treatments of dry eye. The model exacerbates the signs and symptoms of dry eye (e.g., corneal staining and ocular discomfort) in a controlled manner by regulating humidity, temperature, airflow, lighting conditions and visual tasking within the CAE chamber. More details are available at www.oraclinical.com/ophthalmic-models/cae.

As used herein, the term "cream" can refer to a thick (high viscosity) liquid or semi-liquid that can be used for therapeutic treatment of a disease, syndrome, or condition (i.e., DES).

The term "dosage" is intended to encompass a formulation expressed in terms of total amounts for a given timeframe, for example as µg/kg/hr, µg/kg/day, mg/kg/day, or mg/kg/hr. The dosage is the amount of an ingredient administered in accordance with a particular dosage regimen. A "dose" is an amount of an agent administered to a mammal in a unit volume or mass, e.g., an absolute unit dose expressed in mg of the agent. The dose depends on the concentration of the agent in the formulation, e.g., in moles per liter (M), mass per volume (m/v), or mass per mass (m/m). The two terms are closely related, as a particular dosage results from the regimen of administration of a dose or doses of the formulation. The particular meaning in any case will be apparent from context.

As used herein, "dry eye" or "dry eye syndrome" or "DES" can refer to an ophthalmic syndrome or ocular surface condition. The Dry Eye WorkShop (DEWS) has redefined dry eye as "a multifactorial disease of the tears and ocular surface that results in symptoms of discomfort, visual disturbance, and tear film instability with potential damage to the ocular surface, accompanied by increased osmolarity of the tear film and inflammation of the ocular surface." Dry eye and tear film instability can damage the ocular surface. It is accompanied by increased osmolarity of the tear film and inflammation of the ocular surface. The tear film instability can be initiated by several etiologies such as xerophthalmia, ocular allergy, topical preservative use and contact lens wear. The tear film instability can cause surface hyperosmolarity.

As used herein, an "effective amount" or "therapeutically effective amount" is that amount sufficient to affect a desired biological effect, such as beneficial results, including clinical results. As such, an "effective amount" depends upon the context in which it is being applied. An effective amount can vary according to factors known in the art, such as the disease state, age, sex, and weight of the individual being treated. Several divided doses can be administered daily or the dose can be proportionally reduced as indicated by the exigencies of the therapeutic situation. In addition, the compositions/formulations of this disclosure can be administered as frequently as necessary to achieve a therapeutic amount.

As used herein, the term "fluorescein staining" can refer to a method of instilling a fluorescein dye into an eye. The fluorescein dye can be instilled either as a liquid drop or via a fluorescein impregnated paper strip. The fluorescein can penetrate in adjoining bowman's and stromal layers, and the dye makes contact with an alkaline interstitial fluid. Fluid turns bright green owing to its pH indicator properties & depending to extent of lesion. The fluorescein cannot stain intact corneal epithelium but can stain corneal stroma, thus demarcating the area of the epithelial loss. The corneal fluorescein staining can stain all corneal damage non-specifically, irrespective of cause (e.g., refractive laser surgery and drug toxicity). For example and not limitation, 2% preservative-free sodium fluorescein solution can be instilled into the inferior conjunctival cul-de-sac of each eye. In order to achieve maximum fluorescence, the examiner should wait several minutes after instillation before evaluating fluorescein staining. A yellow filter can be used to enhance the ability to grade fluorescein staining. The staining will be graded with the Fluorescein Staining Scale. Digital images of fluorescein staining can be taken for digital analysis. In some embodiments, lissamine green solution can be instilled into the inferior conjunctival cul-de-sac for staining.

As used herein, the term "fragment" or "peptide" or "peptide fragment" comprises a portion of a protein (e.g., Tβ4 protein) with homology or percent amino acid sequence identity. Peptides can be biologically occurring short chains of amino acid monomers linked by peptide (amide) bonds.

As used herein, "gel" can refer to a material which is not a readily flowable liquid and is not a solid, i.e., a semi-solid gel. Gels can be formed from naturally occurring or synthetic materials. The gels can be non-ordered to slightly ordered showing some birefringence, liquid crystal character. A semi-solid gel formulation apparent viscosity can increase with concentration. Gels can be administered topically.

As used herein, "homology" or "percent (%) amino acid sequence identity" is used with respect to a protein (i.e Tβ4 or fragment thereof). The homology or percent amino acid sequence identity can be defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity (i.e., about 60% identity, preferably 61%, 62%, 63%, 64%, 65%, 66%, 6'7%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical". This definition also refers to, or can be applied to, the compliment of a test sequence. The definition also includes sequences that have deletions and/or additions, as well as those that have substitutions. Alignment for purposes of determining percent amino acid sequence identity can be achieved in various ways that are within the skill in the art, for instance, using publicly available computer software such as BLAST, BLAST-2 or ALIGN software. Those skilled in the art can determine appropriate parameters for measuring alignment, including any algorithms needed to achieve maximal alignment over the full length of the sequences being compared.

As used herein, "intermittent administration" includes the administration of a composition for a period of time (which can be considered a "first period of administration"), followed by a time during which the composition is not taken or is taken at a lower maintenance dose (which can be considered an "off-period") followed by a period during which the composition is administered again (which can be considered a "second period of administration"). Generally, during the second phase of administration, the dosage level of the composition will match that administered during the first period of administration but can be increased or decreased as medically necessary.

As used herein, "liquid" is a dosage form consisting of a composition in its liquid state. A liquid is pourable; it flows and conforms to its container at room temperature. Liquids display Newtonian or pseudoplastic flow behavior. In certain embodiments, a "semi-liquid" as used herein can have properties of both a liquid and another formulation (i.e., a suspension, an emulsion, a solution, a cream, a gel, a jelly, and the like).

As used herein, "ocular surface" includes the cornea and the conjunctiva. The ocular surface is covered by a thin layer of fluid or tear film. The tear film is not only responsible for the majority of the refractive power of the eye and clear vision; it is also responsible for nourishing the cells on the surface of the eye and preventing infection. The surface of the eye can suffer many kinds of diseases. One of most common diseases of the surface of the eye is DES.

As used herein, "ocular surface disorder" "ophthalmic disease," "ophthalmic disorder," and the like, includes, but is not limited to, dry eyes, epithelial defects, Superior limbic keratoconjunctivitis, keratoconjunctivitis sicca, Neurotrophic keratopathy, Sjögren's syndrome, Stevens-Johnson syndrome, Ocular cicatricial pemphigoid, Medicamentosa, Graft-versus-host disease, and corneal ulcerations and erosions.

As used herein, "ointment" can refer to a highly viscous liquid or semi-liquid formulation that can be used for therapeutic treatment of a disease, syndrome, or condition (i.e., DES).

As used herein, "ophthalmic composition" refers to a composition intended for application to the eye or its related or surrounding tissues such as, for example, the eyelid or onto the surface of eye. The term also includes compositions intended to therapeutically treat conditions of the eye itself or the tissues surrounding the eye. The ophthalmic composition can be applied topically or by other techniques, known to persons skilled in the art, such as injection to the eye. Examples of suitable topical administration to the eye include administration in eye drops and by spray formulations. A further suitable topical administration route is by subconjunctival injection.

As used herein, "Fluorescein Staining Scale" refers to a scale specific to dry eye to for grading. Corneal staining can be assessed, for example, in the inferior, central, and superior regions of the cornea. Conjunctiva staining is assessed, for example, in the temporal and nasal regions of the conjunctiva. Grading by the clinician normally involves a qualitative estimation of punctate dots in various corneal regions. The cornea and conjunctiva are typically divided into several regions (e.g., inferior, superior, central, temporal, nasal) with each region graded separately. The Fluorescein Staining Scale ranges from 0 to 4 (half grade increments can be used), where grade 0=none and 4=severe.

As used herein, "Ocular Discomfort Scale" refers to a scale specific to measuring ocular discomfort levels of dry eye for grading. Ocular discomfort scores can be subjectively graded by the subjects according to the following scale, rating each eye separately. It consists of a 5-point scale ranging from 0 to 4, where grade 0=no discomfort and 4=severe discomfort. Relatively higher symptomatic subjects can include subjects with an ocular discomfort score of 2 or 3, whereas relatively lower symptomatic subjects can have an ocular discomfort score of 0 or 1.

As used herein, "patient," "patient in need thereof," "subject," and "subject in need thereof" are used interchangeably and refer to an animal or living organism (human or nonhuman) suffering from or prone to a disease or condition that can be treated by administration using the methods and compositions provided herein. Non-limiting examples of subjects include humans, other mammals, bovines, rats, mice, dogs, monkeys, goat, sheep, cows, deer, and other non-mammalian animals. In certain embodiments, the subject is human.

As used herein, "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. Pharmaceutically acceptable carriers include sterile aqueous solutions or dispersions and sterile powders for the extemporaneous preparation of sterile topical solutions or dispersion. The use of such media and agents for pharmaceutically active substances is well known in the art. Except insofar as any conventional media or agent is incompatible with the composition (e.g., Tβ4 or fragments thereof), use thereof in the ophthalmic compositions for the disclosure is contemplated.

The term, "preservative" as used herein can include any agents included in an ophthalmic composition for the purpose of inhibiting the growth of microorganisms (e.g., bacteria, fungi, viruses, and protozoa) in the product, thereby helping to maintain sterility during use. Additionally, the term "anti-microbial agent" can be used herein to denote a specific active agent which provides the antimicrobial efficacy. Exemplary preservatives can include, for example, benzalkonium chloride, thimerosal, chlorobutanol, chlorhexidine, methyl paraben, propyl paraben, phenylethyl alcohol, edetate disodium sorbic acid, Onamer M Polyquat, cetyl bromide, cetyl pyridinium chloride, benzyl bromide, EDTA, phenylmercury nitrate, phenylmercury acetate, thimerosal, merthiolate, acetate and phenylmercury borate, polymyxin B sulphate, methyl and propyl parabens, quaternary ammonium chloride, sodium benzoate, sodium proprionate, and sodium perborate, and other agents known to those skilled in the art, or a combination thereof.

As used herein, the terms "prevent," "preventing," or "prevention," "prophylactic treatment" and the like, refer to reducing the probability of developing a disorder or condition in a subject, who does not have, but is at risk of or susceptible to developing a disorder or condition. The prevention can be complete (i.e., no detectable symptoms) or partial, so that fewer symptoms are observed than would likely occur absent treatment. The terms further include a prophylactic benefit. For a disease or condition to be prevented, the compositions can be administered to a patient at risk of developing a particular disease, or to a patient reporting one or more of the physiological symptoms of a disease, even though a diagnosis of this disease cannot have been made.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 can include 1 to 10, 1 to 20, 1 to 30, and 1 to 40 in one direction, or 50 to 40, 50 to 30, 50 to 20, and 50 to 10 in the other direction.

As used herein "Schirmer's test" refers to a test used to determine whether the eye produces enough tears to keep it moist. For example, the Schirmer's test can be performed according to the following procedure: (a) a sterile Schirmer's test strip will be placed in the lower temporal lid margin of each eye such that the strip fits tightly. Subjects will be instructed to close their eyes and (b) after 5 minutes have elapsed, the Schirmer strip will be removed. The length of the moistened area will be recorded (mm) for each eye. This test is used when a person experiences very dry eyes or excessive watering of the eyes and poses no risk to the subject. A negative (more than 10 mm of moisture on the filter paper in 5 minutes) test result is normal.

As used herein, "sequential administration" includes that the administration of two agents (e.g., compositions described herein) occurs separately on the same day or do not occur on a same day (e.g., occurs on consecutive days).

As used herein, a "solution" is a clear, homogeneous liquid dosage form that contains one or more chemical substances (i.e., Tβ4 or fragments thereof) dissolved in a solvent or mixture of mutually miscible solvents. A solution is a liquid preparation that contains one or more dissolved chemical substances in a suitable solvent or mixture of mutually miscible solvents. Because molecules of a drug substance in solution are uniformly dispersed, the use of solutions as dosage forms generally provides assurance of uniform dosage upon administration and good accuracy when the solution is diluted or otherwise mixed. For example and not limitation, Tβ4 can be dissolved in a solution comprised of sodium chloride, potassium chloride, calcium chloride, magnesium chloride, sodium acetate, and sodium citrate, with a pH of approximately 7.0.

The term "solvent," as used herein, refers to a liquid solvent either aqueous or non-aqueous. The selection of the solvent depends notably on the solubility of the composition on said solvent and on the mode of administration. Aqueous solvent can consist solely of water, or can consist of water plus one or more miscible solvents, and can contain dissolved solutes such as sugars, buffers, salts or other excipients. The more commonly used non-aqueous solvents are the short-chain organic alcohols, such as, methanol, ethanol, propanol, short-chain ketones, such as acetone, and poly alcohols, such as glycerol.

"Suspension," as used herein, is a liquid dosage form that contains solid particles dispersed in a liquid vehicle.

As used herein, the term "syndrome" can refer to a group of symptoms that consistently occur together or a condition characterized by a set of associated symptoms. A syndrome (e.g., DES) can be a set of medical signs and symptoms that are correlated with a specific disease. A disease on the other hand, can be a health condition that has a clearly defined reason behind it. A syndrome (from the Greek word meaning 'run together') however, can produce a number of symptoms without an identifiable cause. They can suggest the possibility of an underlying disease or even the chances of developing a disease.

As used herein, the terms "tear breakup time" or "TBUT" or "tear film breakup time" or "TFBUT" can refer to a clinical test that measures the interval between the individual's last complete blink and the breakup of the tear film. The test can be used to assess for DES. To measure TBUT, fluorescein is instilled into the patient's tear film and the patient is asked not to blink while the tear film is observed under a broad beam of cobalt blue illumination. The TBUT is recorded as the number of seconds that elapse between the last blink and the appearance of the first dry spot in the tear film.

As used herein, "tear film" can refer to a three-layered structure, comprising a mucoidal basal layer, an aqueous component and a superficial lipid layer. The components work together to maintain the overall form of tear film. The tear film is formed and maintained by blinking. The structure of the tear film can be affected by systemic or ocular medication, general health and a number of ocular conditions, such as keratoconjunctivitis sicca or DES. The tears are also affected by age, with changes in both the volume of tear production and stability of the tear film. Patients with relatively lower tear film stability can refer to patients with a tear film break up time shorter than the median value of a total population. Patients with relatively higher tear film stability can refer to patients with a tear film break up time longer than the median value of a total population.

As used herein, "thymosin beta 4" or "Tβ4" refers to a human protein. Tβ4 encodes for an actin sequestering protein which plays a role in regulation of actin polymerization. The protein is also involved in cell proliferation, migration, and differentiation. The thymosin beta 4 peptide, if used after a heart attack, has been shown to potentially reactivate cardiac progenitor cells to repair damaged heart tissue. The safety of topical Tβ4 formulations has been demonstrated, both in dermal preparations and in a preservative-free formulation used in the eye. Based on its multifunctional activities during tissue regeneration, Tβ4 has the potential for clinical application in a wide range of pathological conditions including ocular surface diseases. The NCBI Reference Sequence of human Tβ4 is available under accession number NP_066932.1.

The terms "treat," "treating" or "treatment," and other grammatical equivalents as used herein, include alleviating, abating, ameliorating, or preventing a disease, condition or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder.

As used herein, "viscosity" refers to a fluid's resistance to flow. Exemplary viscosity agents that can be used include, for example polyvinyl alcohol, polyvinyl pyrrolidone, methyl cellulose, hydroxy propyl methylcellulose, hydroxyethyl cellulose, carboxymethyl cellulose, hydroxy propyl cellulose, other agents known to those skilled in the art, or a combination thereof.

As used herein, the term "weight percent" or "% (w/w)" refers to a percentage of a component in a solution that is calculated on the basis of weight for the component and the solvent. For example, a 1% (w/w) solution of a component would have 1 g of the component dissolved in a 100 g of solvent. The term "volume percent" or "% (v/v)" refers to a percentage of a component in a solution that is calculated on the basis of volume for the component and the solvent. For example, a 1% (v/v) solution of a component would have 1 mL of the component dissolved in a 100 mL of solvent. The term "weight/volume percent" or "% (w/v)" refers to a percentage of a component in a solution that is calculated on the basis of weight for the component and on the basis of volume for the solvent. For example, a 1.0% (w/v) solution of a component would have 1 g of the component dissolved in a 100 mL of solvent.

Compositions

The present disclosure provides for ophthalmic compositions comprising Tβ4 or fragments thereof, in an effective amount to treat DES and symptoms thereof in a subject in need thereof.

In certain embodiments, the ophthalmic composition can include from about 0.05% to about 0.1% by weight of Tβ4 or fragments thereof. Human Tβ4 is a polypeptide composed of 43 amino acids having 4.9 kDa, which can be first isolated from thymus and then identified from various tissues. This protein can upregulate the migration and proliferation of corneal epithelial cells. In some embodiments, the ophthalmic composition can include Tβ4 isoforms. Tβ4 isoforms can have about 70%, or about 75%, or about 80% or more homology to the known amino acid sequence of Tβ4. Such isoforms can include, for example, TOO', Tβ9, Tβ10, Tβ11, Tβ12, Tβ13, Tβ14 and Tβ15. Tβ4 of the presently disclosed subject matter can also be an N-terminal variant or C-terminal variant of wild-type Tβ4.

In certain embodiments, the ophthalmic composition can include a peptide agent comprising amino acid sequence LKKTET [SEQ ID NO:1] or LKKTNT [SEQ ID NO:2], or a conservative variant thereof. Amino acid sequence, LKKTET [SEQ ID NO:1] and LKKTNT [SEQ ID NO:2] appear to be involved in mediating actin sequestration or binding. Tβ4 has anti-inflammatory activity, and can also modulate actin polymerization (e.g. β-thymosins appear to depolymerize F-actin by sequestering free G-actin). Tβ4's ability to modulate actin polymerization can be due to its ability to bind to or sequester actin via the LKKTET [SEQ ID NO:1] or LKKTNT [SEQ ID NO:2] sequence. Thus, as with Tβ4, other proteins which are anti-inflammatory and/or bind or sequester actin, or modulate actin polymerization, including Tβ4 isoforms having the amino acid sequence LKKTET [SEQ ID NO:1], are likely to be effective, alone or in a combination with Tβ4, as set forth herein. For example and not limitation, other agents or proteins having anti-inflammatory activity and/or actin sequestering or binding capability, or that can mobilize actin or modulate actin polymerization, as demonstrated in an appropriate sequestering, binding, mobilization or polymerization assay, or identified by the presence of an amino acid sequence that mediates actin binding, such as LKKTET [SEQ ID NO:1] or LKKTNT [SEQ ID NO:2], for example, can similarly be employed in the disclosed subject matter. Such proteins can include gelsolin, vitamin D binding protein (DBP), profilin, cofilin, depactin, Dnasel, vilin, fragmin, severin, capping protein, β-actinin and acumentin.

In certain embodiments, the ophthalmic composition can include oxidized forms of Tβ4 including Tβ4 sulfoxide or conservative variant thereof. Oxidized Tβ4 is a form of Tβ4 in which a methionine residue, 6 amino acids from the N-terminus (Met6), is oxidized such that the residue is converted to methionine sulfoxide. The oxidized Tβ4 can be obtained by reacting native Tβ4 under oxidizing conditions, for example, by treating with hydrogen peroxide.

Although the present invention is described primarily hereinafter with respect to Tβ4 and Tβ4 fragments, it is to be understood that the following description is intended to be equally applicable to amino acid sequence LKKTET [SEQ ID NO:1] or LKKTNT [SEQ ID NO:2], peptides and fragments comprising or consisting essentially of LKKTET [SEQ ID NO:1] or LKKTNT [SEQ ID NO:2], conservative variants thereof and/or Tβ4 isoforms, analogues or derivatives, including oxidized Tβ4, N-terminal variants of Tβ4, and C-terminal variants of Tβ4.

In certain embodiments, the ophthalmic composition can include carriers which can be suitable for topical or intravitreal administration. The carriers can include, for example and not limitation, water; a mixture of water and water-miscible solvents such as $C_1$-$C_7$ alkanols, vegetable oils or mineral oils such as from about 0.5 to about 5 wt. % of hydroxyethyl cellulose, ethyl oleate, carboxymethyl cellulose, polyvinyl pyrrolidone, and other non-toxic water-soluble polymers for ophthalmic use, for example, cellulose derivatives such as methyl cellulose, alkali-metal salts of carboxymethyl cellulose, hydroxymethyl cellulose, hydroxyethyl cellulose, hydroxypropyl methyl cellulose and hydroxypropyl cellulose, acrylates or methacrylates such as salts of polyacrylate or ethyl acrylate, polyacrylamides; natural products such as gelatin, alginate, pectin, tragacanth, karaya gum, xanthan gum, carrageenan, agar, acacia, starch derivatives such as starch acetate and hydroxylpropyl starch; and other synthetic products, for example, polyvinyl alcohol, polyvinyl pyrrolidone, polyvinyl methylether, polyethylene oxide, preferably, cross-linked polyacrylic acid such as neutral carbopol, or mixtures of the above polymers. Preferable carriers can include water, cellulose derivatives, for example, methyl cellulose, alkali-metal salts of carboxymethyl cellulose, hydroxymethyl cellulose, hydroxyethyl cellulose, hydroxypropyl methyl cellulose and hydroxypropyl cellulose, neutral carbopol, or mixtures thereof.

In certain embodiments, the ophthalmic composition can include one or more a pharmaceutically acceptable excipients including but not limited to stabilizers, buffers, preservatives, tonicity agents, and viscosity enhancers.

In certain embodiments, the ophthalmic composition can include stabilizers. The stabilizers according to the presently disclosed subject matter can include, for example and not limitation, tyloxapol, aliphatic glycerol poly-lower alkylene glycol esters, aliphatic poly-lower alkylene glycol esters, polyethylene glycols, glycerol ethers, acetic acid, citric acid, ascorbic acid, EDTA/disodium edetate, glutathione, acetylcysteine or mixtures of these compounds. Acetic acid used herein is a weak acid represented by formula $CH_3COOH$. In the presently disclosed subject matter, this can be used in the form of an acetate. The acetate can include at least one molecule of water. For example and not limitation, mono-, sesqui-, di-, tri-, tetra-, penta-, hexa-, hepta-, octa-, nona-, deca-, undeca-, or dodeca-hydrate forms of acetate can be added into the composition. In particular, sodium acetate trihydrate can be included in an amount of from about 0.01% (w/v) to about 1.5% (w/v) based on the total volume of the composition. Further, acetic acid or its salt can be included in an amount of from about 0.1% (w/v) to about 0.8% (w/v), and preferably, from about 0.2% (w/v) to about 0.5% (w/v). Citric acid used herein is a compound represented by formula $C_6H_8O_7$. In the presently disclosed subject matter, citric acid can be used in the form of one or more citrates. The citrate can be a derivative of citric acid. Additionally, the citrate can include at least one molecule of water. For example and not limitation, mono-, sesqui-, di-, tri-, tetra-, penta-, hexa-, hepta-, octa-, nona-, deca-, undeca-, or dodeca-hydrate forms of citrate can be added into the composition. In particular, the citrate can be sodium citrate and sodium citrate trihydrate. In this case, citric acid or its salt can be included in an amount of from about 0.01% (w/v) to about 0.5% (w/v). Further, citric acid or its salt can be included in an amount of from about 0.05% (w/v) to about 0.25% (w/v), and preferably, from about 0.1% (w/v) to about 0.3% (w/v). They are typically added in an amount sufficient to dissolve active ingredients.

In certain embodiments, the ophthalmic composition can include a buffer. For example, the buffer can include any forms of acetate, ascorbate, borate, hydrocarbonate/carbonate, gluconate, phosphate, propionate, acetic acid, citric acid and/or tromethamine (TRIS) buffers. The buffer can be added, for example, in an amount to ensure and maintain a physiologically acceptable pH range. Such pH can be typically in the range of about 5 to about 9, preferably from about 6 to about 8.2, more preferably from about 6.8 to about 8.1.

In other embodiments, the pH value of the ophthalmic formulations can range from about 3.5 to about 9, preferably from about 4.5 to about 8, and most preferably from about 5.5 to about 7.8, and can be about pH 7.0.

The composition in accordance with the presently disclosed subject matter can further include an acid selected from the group consisting of hydrochloric acid, acetic acid, phosphoric acid etc. The composition can further include a base selected from the group consisting of sodium hydroxide, potassium hydroxide, sodium hydrogen carbonate etc., specifically, sodium hydroxide. For example and not limitation, hydrochloric acid or sodium hydroxide can be suitably added to adjust a pH of the composition. As such, the pH of the composition can be from about 6.5 to about 7.5, or from about 6.8 to about 7.2. Preferably, the composition can have a pH of about 7.0.

In certain embodiments, the ophthalmic composition can include preservatives. The preservatives can include, for example, quaternary ammonium salts such as Cetrimide, benzalkonium chloride or benzoxonium chloride; alkyl-mercury salts of thiosalicylic acid such as thimerosal, phenylmercuric nitrate, phenylmercuric acetate or phenylmercuric borate, parabens such as phenylparaben or propylparaben, alcohols such as chlorobutanol, benzyl alcohol or phenyl ethanol, guanidine derivatives such as chlorohexidine or polyhexamethylene biguanide or sorbic acid. Preferable preservatives can include cetrimide, benzalkonium chloride, benzoxonium chloride and parabens. The preservative can be added in a sufficient amount to prevent secondary contamination caused by bacteria and fungi during the use.

In certain embodiments, the ophthalmic composition can include a tonicity agent to adjust the composition closer to isotonicity (e.g., 0.9% saline). For instance and not limitation, any form of sodium chloride, potassium chloride, calcium chloride, magnesium chloride, dextrose and/or mannitol can be added to the composition comprising thymosin β4 according to the presently disclosed subject matter. The tonicity agents can include at least one molecule of water. For example and not limitation, mono-, sesqui-, di-, tri-, tetra-, penta-, hexa-, hepta-, octa-, nona-, deca-, undeca-, or dodeca-hydrate forms of sodium chloride, potassium chloride, calcium chloride and/or magnesium chloride can be added into the composition. An amount of the tonicity agent depends upon the kind of active agents to be added. In general, particular compositions of the present disclosed subject matter can include a tonicity agent therein to enable the final composition to have an osmolality acceptable for ophthalmic use, i.e., preferably in a range of from about 150 to about 450 mOsm, and more preferably in a range of from about 250 to about 350 mOsm. Preferable tonicity agents can include, for example, sodium salts and potassium salts, in particular, sodium chloride and potassium chloride.

Most preferably, the tonicity agent can be sodium chloride. Further, a concentration of sodium chloride can range from about 0.1 to about 1.2% (w/v) or from about 0.3 to about 1.0% (w/v). Preferably, it ranges from about 0.5 to about 0.7% (w/v). Further, a concentration of potassium chloride can range from about 0.01 to about 0.15% (w/v) or from about 0.03 to about 0.12% (w/v). Preferably, it ranges from about 0.05 to about 0.09% (w/v). Further, a concentration of calcium chloride dihydrate can range from about 0.01 to about 0.12% (w/v) or from about 0.03 to about 0.09% (w/v). Preferably, it ranges from about 0.03 to about 0.06% (w/v). Further, a concentration of magnesium chloride hexahydrate can range from about 0.01 to about 0.12% (w/v), and preferably, from about 0.01 to about 0.05% (w/v). Although the tonicity agents are described primarily herein with respect to adjusting tonicity of the ophthalmic composition, the disclosed tonicity agents can also be used as electrolytes.

In certain embodiments, the ophthalmic composition can include a viscosity enhancer. Suitable viscosity enhancers in ophthalmic formulations and their concentration ranges used in certain inventive compositions can include but are not limited to: (a) Monomeric polyols, such as tyloxapol (from about 0.1 to about 1%), glycerol (from about 0.2 to about 1%), propylene glycol (from about 0.2 to about 1%), ethylene glycol (from about 0.2 to about 1%); (b) Polymeric polyols, such as polyethylene glycol (e.g., PEG 300, PEG 400) (from about 0.2 to about 1%); (c) Cellulose derivatives (polymers of the cellulose family), such as hydroxyethylcellulose (from about 0.2 to about 2.5%), hypromellose (from about 0.2 to about 2.5%), hydroxypropylmethyl cellulose (from about 0.2 to about 2.5%), methylcellulose (from about 0.2 to about 2.5%), carboxymethylcellulose sodium (from about 0.2 to about 2.5%), hydroxylpropylcellulose (from about 0.2 to about 2.5%); (d) Dextrans, such as dextran 70 (at about 0.1% when used with another polymeric demulcent agent); (e) Water-soluble proteins such as gelatin (at about 0.01%), (f) Vinyl polymers such as polyvinyl alcohol (from about 0.1 to about 4%), polyvinyl pyrollidine (from about 0.1 to about 4%); (g) Other polyols, such as polysorbate 80 (from about 0.2 to about 1%), povidone (from about 0.1 to about 2%); (h) Carbomers, such as carbomer 934P, carbomer 941, carbomer 940, and carbomer 974P, and (i) Polysaccharides/Glycosaminoglycans, such as hyaluronan (hyaluronic acid/hyaluronate) (from about 0.1 to about 3%), chondroitin sulfate (from about 0.1 to about 3%).

In certain embodiments, the amount and type of excipient(s) added can be varied depending on specific requirements, the excipient(s) is generally used in a range of about 0.0001 to about 90 wt. %, and within the range commonly used in ophthalmic fields.

In certain embodiments, the ophthalmic composition is formulated as a solution, suspension, semi-liquid, semi-solid gel, gel, ointment or cream. In specific embodiments, the ophthalmic composition can be formulated as a preservative-free, sterile eye-drop solution in a single unit dropper. According to one embodiment the topical formulation containing the active compound can also contain a physiologically compatible vehicle, as those skilled in the ophthalmic art can select using conventional criteria.

In certain embodiments, the ophthalmic composition is administered in the form of eye drops. The ophthalmic composition can be, where appropriate, adjusted and/or buffered to the desired pH and, where appropriate, a stabilizer, or a tonicity enhancing agent can be added. Where appropriate, preservatives and/or other excipients can be added to an ophthalmic composition.

In certain embodiments, the ophthalmic composition can be formulated into a unit dosage form to provide a total daily dosage of from about 0.08 to about 2.0 ml and can be suitably filled in a container for ophthalmic use, which can enable quantitative administration of the composition. For this purpose, the composition can be formulated into a unit dosage form with a dose of from about 0.01 to about 10 ml that can be used once or several times. Further, in order to suitably provide the pharmaceutical composition in a total daily dosage of from about 0.08 to about 2.0 ml, the composition can be contained in an eye drop container dropping from about 0.01 to about 2.0 ml per droplet.

In certain embodiments, the ophthalmic composition can include from about 0.05 to about 0.1% by weight of Tβ4 or fragments thereof. The ophthalmic composition can be in a solution comprised of sodium chloride, potassium chloride, calcium chloride dihydrate, magnesium chloride hexahydrate, sodium acetate trihydrate, and sodium citrate trihydrate. The pH of the composition can be adjusted to about 6.5 to about 7.5 using an acid or a base. The acid can be selected from the group consisting of hydrochloric acid, acetic acid, phosphoric acid, etc. The base can be selected from the group consisting of sodium hydroxide, potassium hydroxide, sodium hydrogen carbonate, etc.

Methods

The present disclosure provides, inter alia, a method of treating DES or signs or symptoms thereof in a subject in need of such treatment. The method includes administering to an eye of the subject an ophthalmic composition including Tβ4 or fragments thereof, in an effective amount to treat DES and signs and symptoms thereof.

The presently disclosed subject matter provides methods that effectively address at least two aspects of DES, including but not limited to inflammatory responses and corneal epithelial healing. In certain embodiments, delivering the ophthalmic composition including Tβ4 or fragments thereof to the dry eye can reduce or prevent inflammation and improve or accelerate corneal epithelial healing. DES can be include various signs and symptoms including, but not limited to, deficient tear production, decreased tear film stability, increased ocular surface damage, and increased ocular discomfort. Subjects with DES can exhibit one or more signs or symptoms. The presently disclosed subject matter effectively treats both inflammatory responses and increases corneal epithelial healing by administering effective amounts of ophthalmic composition including Tβ4 or fragments thereof. Such methods are successful in increasing tear amounts, increasing tear film stability, decreasing ocular surface damage and decreasing ocular discomfort.

In certain embodiments, the method of treating DES includes treating dry eye associated with or resulting from treating inflammation of the surface of the eye, the lacrimal gland, or the conjunctiva; dry eye associated with any disease process that alters the components of the tears; dry eye associated with an increase in the surface of the eye, as in thyroid disease when the eye protrudes forward; and/or dry eye associated with a cosmetic surgery, for example, if the eyelids are opened too widely during surgery; dry eye associated with eye correction surgery such as laser-assisted in situ keratomileusis (LASIK) or laser-assisted sub epithelial keratectomy (LASEK). Hyperosmolarity can cause damage to the surface epithelium by activating a cascade of inflammatory events and releasing inflammatory mediators into the tears. The inflammatory mediators can cause cell death, loss of goblet cells, reduction in mucus secretion, and tear film instability. In certain embodiments, delivering an ophthalmic composition including Tβ4 or fragments thereof to the tear-deficient dry eye can improve tear film stability and/or increase the tear amount. The methods herein can improve the quality of the lacrimal gland which secretes the aqueous layer of the tear film.

The presently disclosed subject matter provides for methods of treating tear-deficient dry eye, which is a disorder in which the lacrimal glands fail to produce enough of the watery component of tears to maintain a healthy eye surface, with a composition of the present disclosure. The aqueous tear-deficient dry eye can be characterized by various assessments, including but not limited to, a tear volume test. The tear volume test can be used to determine whether the eye produces enough tears to keep it moist.

For example and not limitation, the tear volume test can be performed according to the following procedure: (a) a sterile test strip can be placed in the lower temporal lid margin of each eye such that the strip fits tightly. Subjects can be instructed to close their eyes and (b) after an appropriate time (e.g., about 5 minutes) has elapsed, the strip can be removed. The length of the moistened area can be recorded (mm) for each eye. This test can be used when a person experiences very dry eyes or excessive watering of the eyes and poses no risk to the subject. A negative test result is normal, whereby, for example, more than about 10 mm of moisture on the filter paper is recorded.

Alternatively, the aqueous tear-deficient dry eye can be characterized by a phenol red thread test. For example and not limitation, the crimped end of a cotton thread impregnated with phenol red dye can be placed in the inferior conjunctival sac on the temporal side. Phenol red is a pH indicator which exhibits a gradual transition from yellow to red when wetted by tears, due to the alkaline nature of tears (pH 7.4). Subjects can be instructed to close their eyes and the thread can be removed after 15 seconds. The length of the color change on the thread, indicating the length of the thread wetted by the tears, can be measured in millimeters. Wetting lengths should normally be between about 9 mm and about 20 mm. Values of less than about 9 mm have been shown to correlate with subjective symptoms of dryness.

The presently disclosed subject matter also provides for methods of improving tear film stability. Tear film stability can be evaluated by various assessments in the art, including but not limited to a TFBUT analysis. For example and not limitation, 2% preservative-free sodium fluorescein solution can be administered into the inferior conjunctival cul-de-sac of each affected eye. In order to achieve maximum fluorescence, an appropriate waiting period is implemented after instillation before evaluating TFBUT. With the aid of a slit-lamp, the integrity of the tear film can be monitored by noting the time it takes to form micelles from the time that the eye is opened. TFBUT can be measured in seconds using a stopwatch and a digital image recording system for one eye followed by the second eye. A negative test result is normal, whereby more than about 10 seconds of TFBUT is recorded.

Alternatively, tear film stability can be evaluated by a Non-Invasive Break-Up Time (NIBUT) analysis. During a NIBUT analysis, an illuminated grid pattern reflected from the anterior tear surface can be observed without administration of fluorescein solution. During a NIBUT analysis, subjects can be asked to stop blinking until told to restart. The time between the last complete blink and the first indication of pattern break-up can be recorded with a stop-watch.

Further, the presently disclosed subject matter provides for methods of improving damaged ocular surface area. Damaged ocular surface area of the dry eye can be characterized by various assessments in the art, including but not limited to a fluorescein staining analysis. During a fluorescein staining analysis, the damaged ocular surface can be stained with fluorescein compounds. For example and not limitation, 2% preservative-free sodium fluorescein solution can be instilled into the inferior conjunctival cul-de-sac of each eye. In order to achieve maximum fluorescence, a waiting time is implemented after instillation before evaluating fluorescein staining. Grading can involve a qualitative estimation of punctate dots in various corneal regions. The cornea and conjunctiva are typically divided into several regions (e.g., inferior, superior, central, temporal, nasal) with each region graded separately. The scale ranges from 0 to 4 (half grade increments can be used), where grade 0=none and 4=severe). In certain embodiments, the fluorescein compounds can include rose bengal for a fluorescein staining analysis.

Alternatively, damaged ocular surface area of the dry eye can be characterized by a lissamine Green Staining analysis. Lissamine Green can stain ocular surface epithelial cells that are unprotected by mucin or glycocalyx. During a lissamine Green Staining analysis, lissamine green solution can be instilled into the inferior conjunctival cul-de-sac of each eye. The subject can be instructed to blink several times to distribute the lissamine green. The staining will be graded with the same staining scale as a fluorescein staining analysis. Alternative staining techniques in the art can also be used, including for example, Rose Bangal.

The presently disclosed subject matter also provides for methods of reducing ocular discomfort in a subject in need thereof with the administration of an ophthalmic composition including Tβ4 or fragments thereof. In certain embodiments, the method includes ameliorating symptoms including but not limited to stinging or burning of the eye; a sandy or gritty feeling as if something is in the eye; episodes of excess tears following very dry eye periods; a stringy discharge from the eye; pain and redness of the eye; episodes of blurred vision; heavy eyelids; inability to cry when emotionally stressed; uncomfortable contact lenses;

decreased tolerance of reading, working on the computer, or any activity that requires sustained visual attention; and/or eye fatigue.

Indications of ocular discomfort can be characterized and quantified by various assessments known in the art. For example and not limitation, ocular discomfort scores can be subjectively graded by the subjects before, after, or during exposure to an adverse environment. During exposure to the adverse environment, the signs and symptoms of dry eye (e.g., corneal staining and ocular discomfort) are exacerbated in a controlled manner by regulating humidity, temperature, airflow, lighting conditions and visual tasking. The discomfort scale can consist of a 5-point scale ranging from 0 to 4, where grade 0=no discomfort and 4=severe discomfort. Relatively higher symptomatic subjects can include subjects with an ocular discomfort score of 2 or 3, whereas relatively lower symptomatic subjects can have an ocular discomfort score of 0 or 1.

As previously noted, the presently disclosed subject matter provides for the effective treatment of DES and associated signs and symptoms characterized by various assessments including but not limited to a Schirmer's test, a TFBUT test, a fluorescein staining test, decreased tear film stability, increased ocular surface damage, increased ocular discomfort, an ocular discomfort analysis and combinations thereof. In certain embodiments, the target subject can have DES characterized by a tear volume test score of less than about 10 mm in an affected eye. In certain embodiments, the target subject can have DES characterized by a tear film break up time of less than about 10 seconds in an affected eye. In certain embodiments, the target subject can have has DES characterized by a total corneal fluorescein staining score of about 4 or higher in an affected eye. In certain embodiments, the target subject can have DES characterized by an ocular discomfort score of about 2 or higher in the affected eye.

In certain embodiments, the present disclosure provides a method for increasing tear amount and tear film stability. In certain embodiments, the present disclosure provides a method for reducing ocular surface damage. In certain embodiments, the present disclosure provides a method for reducing ocular discomfort. All methods provided herein include the administration of an ophthalmic composition including Tβ4 or fragments thereof to one or both eyes of a subject in need thereof.

Co-Administration

In certain embodiments, the methods of treating DES can be managed as an ongoing condition. In certain embodiments, if there is an underlying disease, that disease is concurrently treated.

In certain embodiments, the composition can be administered at the same time, just prior to, or just after the administration of additional therapies. The composition of the disclosure can be administered alone or can be co-administered with a second composition/therapeutic agent to a subject.

Co-administration can be meant to include simultaneous or sequential administration of the composition individually or in combination with a second composition/therapeutic agent.

In certain embodiments, the method includes treating DES with a composition of the present disclosure in combination with artificial tears. Artificial tears can include any ocular ointments, drops, or sprays and the like known in the art. Exemplary artificial tears can include, for example, Celluvisc, Clear Eyes CLR, GenTeal, Hypotears, Isopto Tears, Lacri-Lube S.O.P., Liquitears, Moisture Drops, Oasis Tears, Opti-Free Rewetting Drops, optive, Refresh, Soothe, Systane, TheraTears, Ultra Fresh, Visine Tears, and the like.

Dosage Regimens

For example and not limitation, the methods can include contacting an eye or eye tissue with an effective amount of a composition including Tβ4 or fragments thereof as an active ingredient. The administration can be topical or intravitreal administration. An example of topical administration can include direct application of the composition in the form of, for example, a solution, lotion, plaster, gel, cream, paste, spray, suspension, dispersion, hydrogel, ointment, oil or foaming agent to a subject in order to contact same with eye tissues In certain embodiments, a method of treating DES in a subject in need thereof, includes administering to an eye of the subject, an ophthalmic composition including human Tβ4 or fragments thereof formulated in the form of a solution, a suspension, a semi-solid gel, a gel, an emulsion, semi-liquid, an ointment, a cream, foam gel, or a controlled-release/sustain-release vehicle. For example, the composition can be in the form of a contact lens solution, eyewash, eye drop, eye gel, eye ointment, and the like.

The following dosage regimens can be used to treat DES in general and can be used to treat both inflammatory responses and increases corneal epithelial healing by administering effective amounts of ophthalmic composition including Tβ4 or fragments thereof. The dosage regimens provided herein can be used to increase tear amounts, increase tear film stability, decrease ocular surface damage and/or decrease ocular discomfort.

In a particular embodiment, the composition is in the form of a solution that can be administered as eye drops. The composition can be administered topically to an eye for treating DES in a dosage range from about 5 µg to about 150 µg per eye, or from about 5 µg to about 100 µg per eye, or from about 5 µg to about 50 µg per eye, or from about 5 µg to about 25 µg per eye. In other embodiments, the composition can be administered topically to an eye for treating DES in a dose range from about 5 µg to about 150 µg per eye, or from about 25 µg to about 150 µg per eye, or from about 50 µg to about 150 µg per eye, or from about 100 µg to about 150 µg per eye.

In certain embodiments, the dosage for one eye can be about 1 to about 5 drops of solution. In certain embodiments, the dosage for one eye can be 1, 2, or 3 drops of solution. Each drop of an ophthalmic composition in solution from can correspond to about 10 µL to about 150 µL of ophthalmic composition. Preferably, each drop of an ophthalmic composition in solution can correspond to about 20 µL to about 70 µL of ophthalmic composition.

In certain embodiments, the ophthalmic composition can be administered to an eye for treating DES by placing one to two drops or more in each eye, 1 to 24 times daily. For example, the ophthalmic composition can be applied, 1, 2, 3, 4, 8, 12, 18 or 24 times a day, or more. In certain embodiments, the ophthalmic composition can be applied by placing one or two drops in each eye, once daily or twice daily, or three times daily, or four times daily. For example and not limitation, the composition can be applied by placing one drop in each eye four times daily, including, for example, in the morning, noon, afternoon, and evening.

In certain embodiments, the method of treating DES includes administering a composition human Tβ4 or fragments thereof to a subject in any suitable or therapeutically effective amount, e.g., from about 0.001 percent by weight to about 90 percent by weight of the composition, from about 0.001 percent by weight to about 1 percent by weight, from about 0.001 percent by weight to about 10 percent by weight, from about 0.001 percent by weight to about 20 percent by weight, from about 0.001 percent by weight to about 30 percent by weight, from about 0.001 percent by weight to about 40 percent by weight, from about 0.001 percent by weight to about 50 percent by weight, from about 0.001 percent by weight to about 60 percent by weight, from about 0.001 percent by weight to about 70 percent by weight, from about 0.001 percent by weight to about 80 percent by weight, from about 0.01 percent by weight to about 90 percent by weight, from about 0.01 percent by weight to about 1 percent by weight, from about 0.01 percent by weight to about 10 percent by weight, from about 0.01 percent by weight to about 20 percent by weight, from about 0.01 percent by weight to about 30 percent by weight, from about 0.01 percent by weight to about 40 percent by weight, from about 0.01 percent by weight to about 50 percent by weight, from about 0.01 percent by weight to about 60 percent by weight, from about 0.01 percent by weight to about 70 percent by weight, from about 0.01 percent by weight to about 80 percent by weight, from about 0.1 percent by weight to about 90 percent by weight, from about 0.1 percent by weight to about 1 percent by weight, from about 0.1 percent by weight to about 10 percent by weight, from about 0.1 percent by weight to about 20 percent by weight, from about 0.1 percent by weight to about 30 percent by weight, from about 0.1 percent by weight to about 40 percent by weight, from about 0.1 percent by weight to about 50 percent by weight, from about 0.1 percent by weight to about 60 percent by weight, from about 0.1 percent by weight to about 70 percent by weight, from about 0.1 percent by weight to about 80 percent by weight, or any range in between, of the composition. In certain embodiments, the method of treating DES includes administering a composition human Tβ4 or fragments thereof to a subject at about 0.05% by weight. In certain embodiments, the method of treating DES includes administering a composition human Tβ4 or fragments thereof to a subject at about 0.1% by weight.

EXAMPLES

The following examples are merely illustrative of the presently disclosed subject matter and they should not be considered as limiting the scope of the disclosed subject matter in any way.

Example 1: Safety and Efficacy of 0.05% and 0.1% Tβ4 Ophthalmic Composition

Study Objectives

The objective of this study was to compare the safety and efficacy of 0.05% Tβ4 ophthalmic composition and 0.1% Tβ4 ophthalmic composition to placebo for the treatment of the signs and symptoms of dry eye.

Materials and Methods

This study was a multicenter, randomized, double-masked study designed to evaluate the efficacy and safety of 0.05% and 0.1% Tβ4 ophthalmic solution compared to placebo in subjects with dry eye. 317 male and female subjects who were at least 18 years of age, had a subject-reported history of dry eye in both eyes and met all other study eligibility criteria were randomized to receive either 0.05% Tβ4, 0.1% Tβ4 or placebo at a ratio of 1:1:1 (105:107:105 subjects in each treatment group, respectively).

The study consisted of two periods: a 7-day run-in period and a 28-day treatment period. A flow chart of the study is presented in FIG. 1.

The CAE is a clinical model that provides a standardized approach to studying investigational treatments of dry eye. The model exacerbates the signs and symptoms of dry eye (e.g. corneal staining and ocular discomfort) in a controlled manner by regulating humidity, temperature, airflow, lighting conditions and visual tasking within the CAE chamber.

Patients and Selection Criteria

Eligible patients were 18 years or older, had a reported history of dry eye for at least 6 months prior to enrollment, and had a history of eye drop use for dry eye symptoms within the previous 6 months. Patients had to have a tear film breakup time (TFBUT)≤10 seconds, unanesthetized Schirmer tear test (mm/5 minutes) of and 10, a sum corneal fluorescein staining score of ≥4, based on the sum of the central, superior, and inferior regions of the cornea with the fluorescein staining scale (reported for each region on a 0-4 scale).

If initial screening requirements were met, patients were required to demonstrate an increase in fluorescein staining following exposure in the CAE. Additionally, patients had to report a worsening in ocular discomfort score (a five-point [0-4] scale, where 0=none and 4=severe) during exposure to the CAE. All patients had to have a corrected visual acuity logarithm of the minimum angle of resolution (log MAR)+ 0.7 in both eyes. Patients who met the selection criteria at visit 1 were initiated on self-administered, placebo solution for 7 days until visit 2 (day 1). After this run-in period, at visit 2, eligible patients were required to meet all assessments as described for visit 1 above.

Interventions

The clinical dosage form and packaging of Tβ4 ophthalmic solution and the placebo ophthalmic solutions were identical sterile, low-density polyethylene unit-dose non-preserved bottles. They were packaged in foil-wrap pouches to prevent light exposure, each containing single-use bottles. Throughout the study, between day 1 and day 29, patients were instructed to instill one drop of study medication in each eye four times daily, once in the morning, noon, afternoon and in the evening before bed. Patients were assigned randomization kit numbers in strict numerical sequence, using a code generated by an independent biostatistician. All investigators, study and site personnel, and patients were masked to the treatment assignments.

Outcome Measures

Patients were evaluated on day 8 (visit 3), day 15 (visit 4), and day 29 (visit 5) during the dosing period. Exposure to the CAE occurred on days 14 and 28. At each study visit, a panel of dry eye signs and symptoms and safety measures were evaluated (including both before [pre-CAE] and after [post-CAE] exposure).

The sign endpoints assessed at each visit, both pre- and post-CAE, included Fluorescein Staining (in three regions: inferior, superior and central cornea, with scores provided in single regions and sum of three regions), TFBUT, and unanesthetized Schirmer's test (measured pre-CAE and/or post-CAE).

The symptom endpoints assessed at each visit (both pre- and post-CAE) were ocular discomfort (Ocular Discomfort Scale, using a five-point [0-4] scale, where 0=none and 4=severe). Ocular discomfort was also graded during exposure to the CAE.

Study Results

Fluorescein Staining Score in Total Cornea Region

Figure 2A:
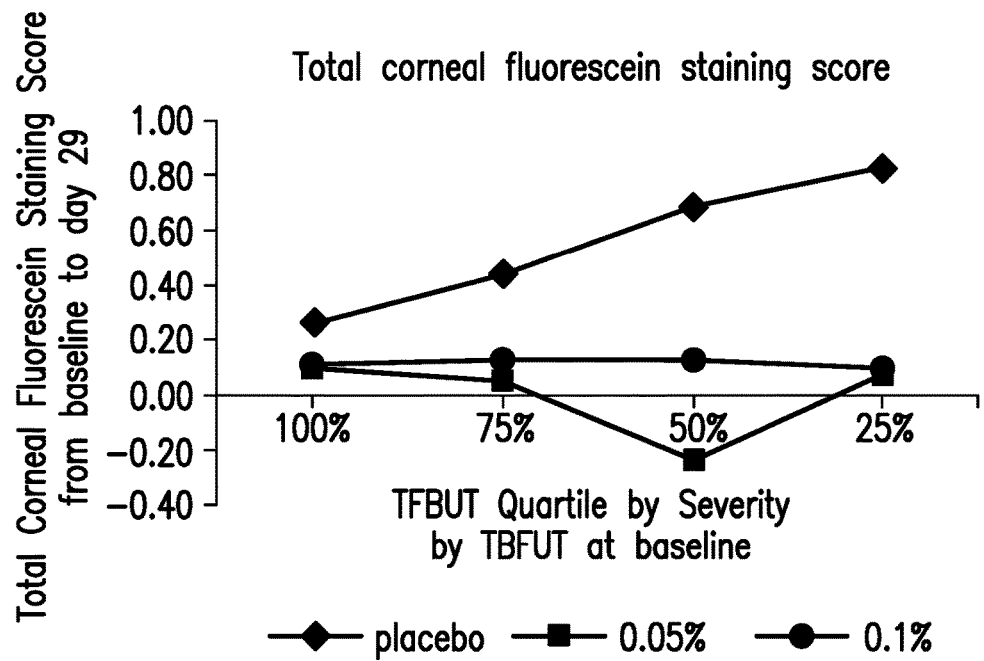
FIGS. 2A and 2B provide (2A) a plot of total cornea fluorescein staining score changes in the 25%, 50%, 75%, and 100% Tear Film Break Up Time (TFBUT) quartile groups and (2B) a plot of total cornea fluorescein staining score changes of the 25% TFBUT quartile group at day 8, day 15, and day 29.

A 28-day treatment (visit 5) with 0.05% and 0.1% Tβ4 elicited improvements on total corneal staining in subjects. Subjects were grouped by the severity of TFBUT at baseline (pre-CAE) and the change of fluorescein staining score for the total cornea from baseline of each sub-group was analyzed. For example, as shown in FIG. 2A, the subjects were grouped into the 100%, 75%, 50%, and 25% quartile groups. As illustrated in FIG. 2A, there was a distinction of the fluorescein staining score between the Tβ4-treated and placebo-treated groups after the 28-day treatment (visit 5) with 0.05% and 0.1% Tβ4 in all quartile groups. For example, when compared with baseline (visit 2) to visit 5, the fluorescein staining score change in total cornea region was 0.83 in placebo group, 0.075 in the 0.05% Tβ4-treated group and 0.10 in 0.1% Tβ4-treated group in the 25% quartile group. The lower fluorescein staining score change indicates less defect in cornea, whereas a high fluorescein staining change indicates the worsening of defect.

Figure 2B:
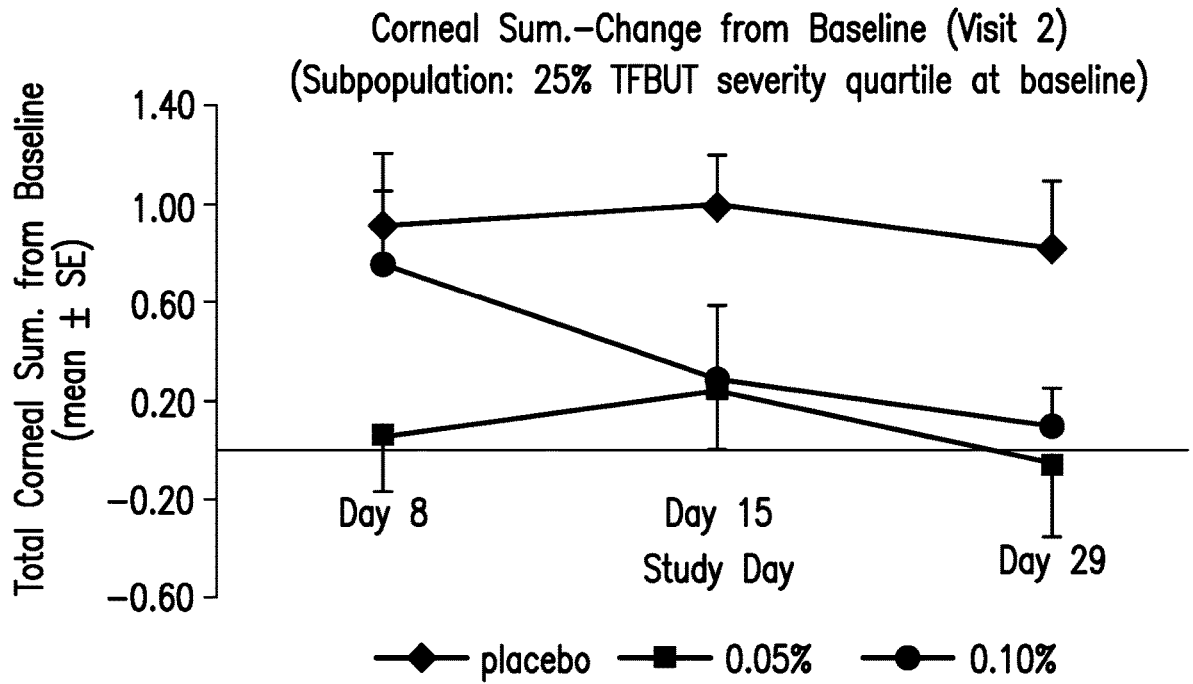

FIG. 2B provides a plot of the change of fluorescein staining score in total cornea region at different time points. The change of fluorescein staining score in total cornea region of the about 25% subpopulation group was measured at day 8 (visit 3), day 15 (visit 4), and day 29 (visit 5). As shown in FIG. 2B, 7-day, 14-day, and 28-day treatments with 0.05% Tβ4 elicited significant improvements on total corneal staining in subjects. Moreover, 14-day and 28-day treatments with 0.1% Tβ4 elicited significant improvements on total corneal staining in subjects.

These results indicated therapeutic effects of the Tβ4 treatment on reducing ocular surface damage of DES patients. Particularly, these results indicated that the Tβ4 treatment can be more effective in patient groups with decreased tear film stability.

Fluorescein Staining Score in Inferior Region

Figure 3A:
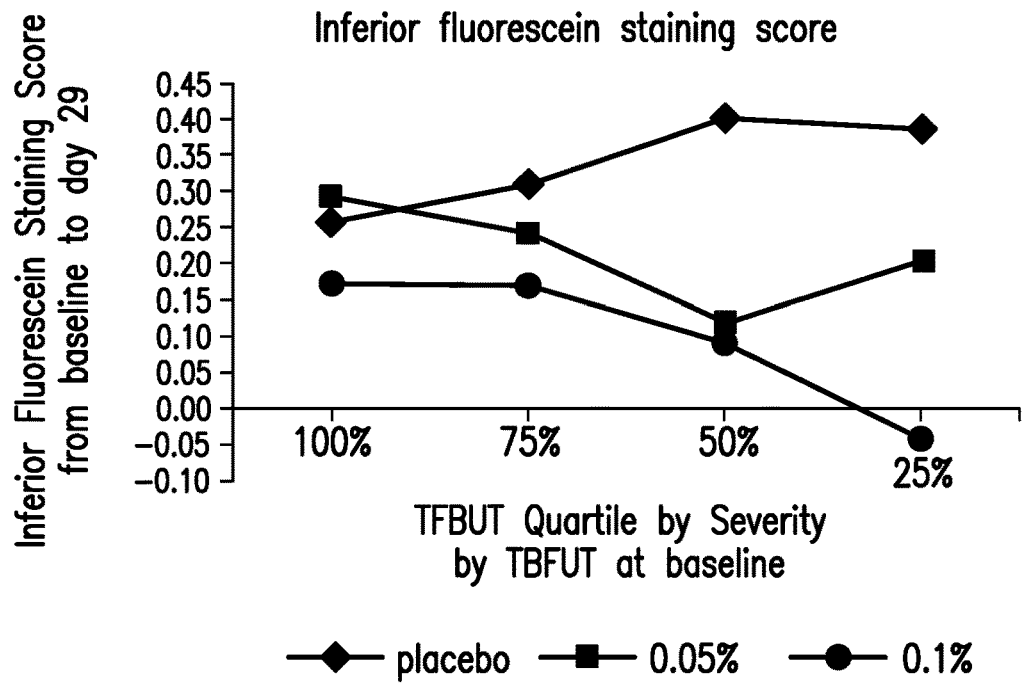
FIGS. 3A and 3B provides (3A) a plot of inferior region fluorescein staining score changes in the 25%, 50%, 75%, and 100% TFBUT quartile groups and (3B) a plot of inferior fluorescein staining score changes of the 50% TFBUT quartile group at day 8, day 15, and day 29.

The 28-day treatment (visit 5) with 0.05% and 0.1% Tβ4 elicited significant improvements on corneal staining in inferior region. Subjects were grouped by the severity of TFBUT at baseline (pre-CAE) as discussed above and the change of fluorescein staining score for the inferior region of cornea from baseline of each sub-group was analyzed. As shown in FIG. 3A, there was a distinction of the fluorescein staining score in inferior region between the Tβ4-treated and placebo-treated groups after the 28-day treatment (visit 5) with 0.05% and 0.1% Tβ4 in 75%, 50%, and 25% quartile groups. For example, when compared with baseline (visit 2) to visit 5, the fluorescein staining score change in inferior region was 0.39 in placebo group, 0.20 in the 0.05% Tβ4-treated group and −0.04 in 0.1% Tβ4-treated group in the 25% subpopulation group.

Figure 3B:
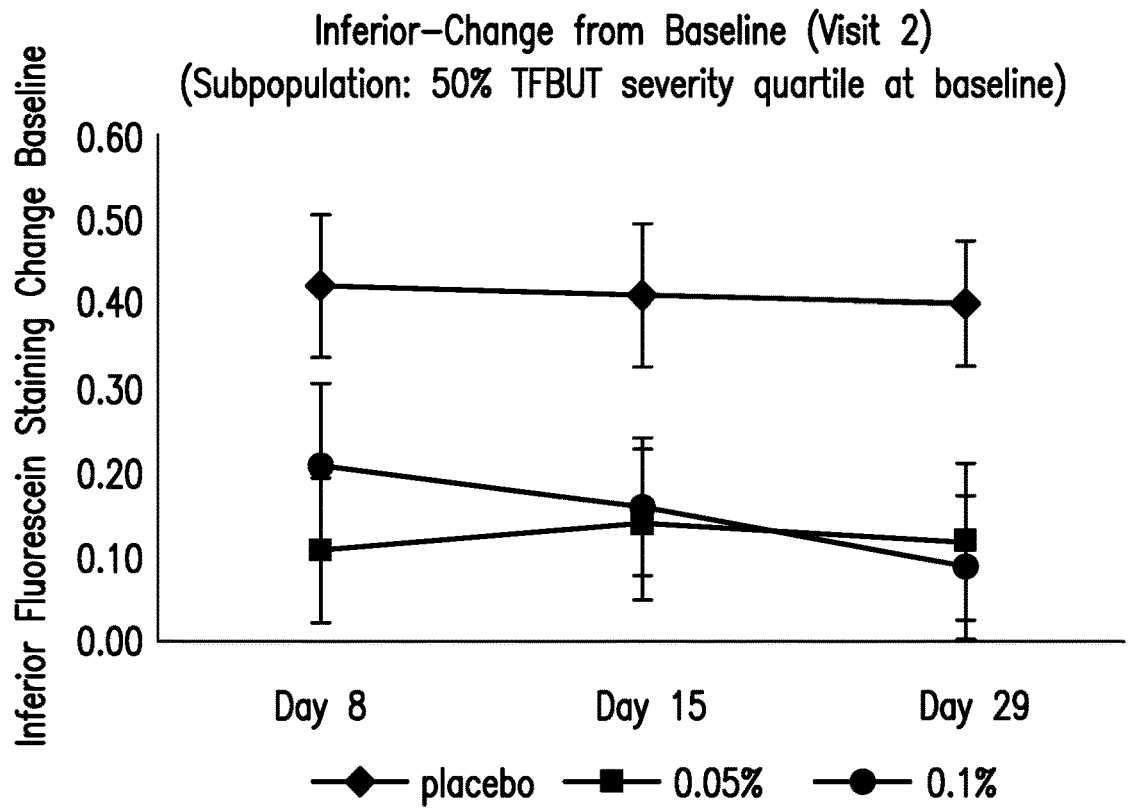

FIG. 3B provides a plot of the change of fluorescein staining score in inferior cornea region at different time points. The change of fluorescein staining score in inferior cornea region of the 50% subpopulation group was measured at day 8 (visit 3), day 15 (visit 4), and day 29 (visit 5). As shown in FIG. 3B, 7-day, 14-day, and 28-day treatments with 0.05% and 0.1% Tβ4 elicited significant improvements on corneal staining in subjects.

The subjects were grouped into the lower tear film stability group and the higher tear film stability group. In the subjects group of the lower tear film stability (the patients had the tear film break up time shorter than the median value of total population) at baseline, there was a distinction between the Tβ4-treated and placebo-treated groups after the 28-day treatment (visit 5) with 0.05% and 0.1% Tβ4. When compared with baseline (visit 2) to visit 5, the fluorescein staining score change in inferior region was 0.400 in placebo group, 0.120 in the 0.05% Tβ4-treated group and 0.009 in 0.1% T04-treated group. The lower fluorescein staining score present the patient indicates less defect in cornea, whereas a high fluorescein staining change indicates the worsening of defect.

In the higher tear film stability group, however (the patients had the tear film break up time longer than the median value of total population) at baseline, the fluorescein staining score change in inferior region from baseline was 0.094 in placebo group, 0.444 in the 0.05% Tβ4-treated group and 0.245 in 0.1% Tβ4-treated group.

When comparing the mean difference between Tβ4-treated group and placebo, the Tβ4-treated groups showed less worsening of defects in the lower tear film stability group than the placebo group (the negative score means the less worsening than placebo group). But in higher tear film stability group, the mean difference between Tβ4-treated group and placebo showed the positive value, i.e., the more worsening of ocular damage.

These results indicated that significant reducing ocular surface damage effect of Tβ4-treated patients with low tear film stability.

TABLE 1

Fluorescein Staining Score in Inferior Region - Change from visit 2 (baseline) to visit 5

| Subpopulation | Lower tear film stability group | | Higher tear film stability group | |
| --- | --- | --- | --- | --- |
| | Subject # | Change from baseline | Subject # | Change from baseline |
| | | Mean | | |
| Placebo | 55 | 0.400 | 48 | 0.094 |
| 0.05% | 50 | 0.120 | 54 | 0.444 |
| 0.1% | 48 | 0.009 | 53 | 0.245 |
| Mean Difference between Tβ4 and Placebo (Tβ4-Placebo) | | | | |
| 0.05% | — | −0.280 | — | 0.350 |
| 0.1% | — | −0.304 | — | 0.141 |

Tear Film Break Up Time

In the subjects group of the lower tear film stability (the patients had the tear film break up time shorter than the median value of total population, e.g., median value between 1-9 seconds) at baseline, there was a distinction between the Tβ4-treated and placebo-treated groups after the 28-day treatment (visit 5) with 0.05% and 0.1% Tβ4. When compared with baseline (visit 2) to visit 5, the tear film break up time change was 0.54 sec in placebo group and 0.74 sec in the Tβ4-treated group. The longer tear film break up time present the patient indicates better tear film stability.

In the higher tear film stability group, however (the patients had the tear film break up time longer than the median value of total population) at baseline, the change from baseline for tear film break up time was 0.05 sec in placebo group and 0.14 sec in the Tβ4-treated group.

When comparing the mean difference between all Tβ4-treated groups and placebo, the mean difference between Tβ4-treated group and placebo showed that the Tβ4 treatment group had the better tear film stability (Tβ4 treatment group vs. placebo=0.20 vs. 0.09).

These results indicated that significant increasing tear film stability effect of Tβ4-treated patients with a low tear film stability.

TABLE 2

Tear Film Break Up Time - Change from visit 2 (baseline) to visit 5

| Subpopulation | Lower tear film stability group | | Higher tear film stability group | |
|---|---|---|---|---|
| | Subject # | Change from baseline (sec) | Subject # | Change from baseline (sec) |
| | Mean | | | |
| Placebo | 55 | 0.54 | 48 | 0.05 |
| Tβ4 | 98 | 0.74 | 106 | 0.14 |
| Mean Difference between Tβ4 and Placebo (Tβ4-Placebo) | | | | |
| Tβ4 | — | 0.20 | | 0.09 |

Ocular Discomfort Score Change During Exposure to the CAE

Figure 4:
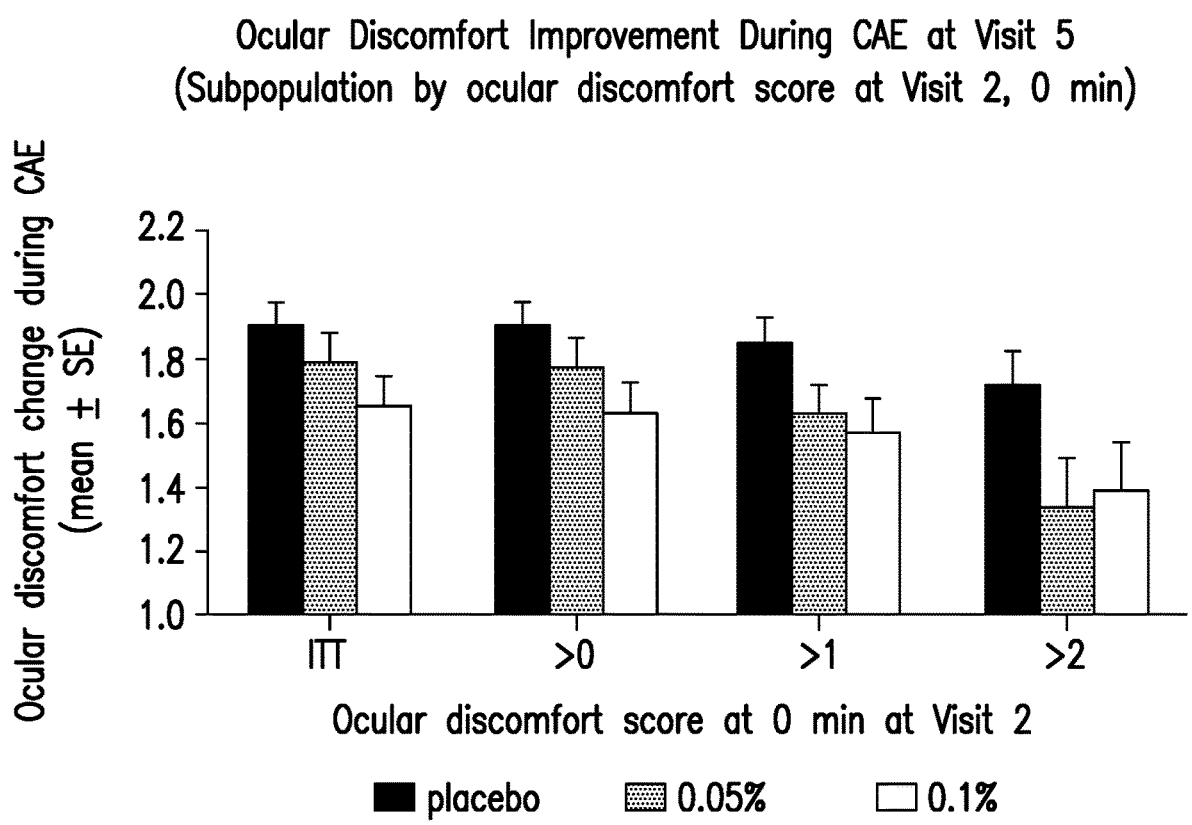
FIG. 4 provides a plot of ocular discomfort during CAE per ocular discomfort at baseline.

The 28-day treatment (visit 5) with 0.05% and 0.1% Tβ4 elicited improvements on ocular discomfort in subjects with dry eye. Subjects were grouped by the severity of ocular discomfort at baseline (beginning of CAE) and the change of ocular discomfort during exposure to the CAE chamber of each sub-group was analyzed. For example, as shown in FIG. 4, the subjects were grouped into the ITT, >0, >1, and >2 subpopulation groups. The ITT subpopulation group included every subject who was randomized. The subjects in the >0 subpopulation group had an ocular discomfort score more than about 0 at visit 2. The subjects in the >1 subpopulation group had an ocular discomfort score more than about 1 at visit 2. The subjects in the >2 subpopulation group had an ocular discomfort score more than about 2 at visit 2. As shown in FIG. 4, following the 28-day treatment with 0.05% and 0.1% Tβ4, there was a distinction between the active and placebo treatment group in all subpopulation groups. Particularly, the ocular discomfort score change from the beginning to the end of CAE was 1.7 in placebo group of the >2 subpopulation. However, the ocular discomfort score change was only 1.34 in the 0.05% Tβ4-treated group and 1.39 in the 0.1% Tβ4-treated group. Comparison of the changes shows a lower increase for 0.1% and 0.05% Tβ4-treated subjects than placebo-treated subjects.

The subjects were grouped into the higher symptomatic subjects group and the lower symptomatic subjects group, based on predetermined ocular discomfort scores. In the higher symptomatic subjects group (a subject had an ocular discomfort score of 2 or 3) at baseline, a distinction between the Tβ4-treated and placebo-treated treatment groups after the 28-day treatment (visit 5) with Tβ4 was observed. When compared with baseline (visit 2) to visit 5, the ocular discomfort score change from the beginning to the end of CAE was 0.50 in placebo group, 0.23 in the 0.05% Tβ4-treated group and 0.06 in 0.1% Tβ4-treated group. The lower ocular discomfort score indicates discomfort, and the low ocular discomfort change indicates a high dampening effect (a protective effect) to the exacerbating condition.

The lower symptomatic subject group (subject had ocular discomfort score 0 and 1) at baseline (visit 2), when compared with baseline (visit 2) to visit 5, the ocular discomfort score change from the beginning to the end of CAE was −0.86 in placebo group, −0.05 in the 0.05% Tβ4-treated group and −0.61 in 0.1% Tβ4-treated group.

These results indicated that Tβ4 treatment caused a significant dampening of the effect of Tβ4 to the CAE, i.e., a protective effect against adverse stimuli, in ocular discomfort change during CAE. The change in response from visit 2 to visit 5 was significantly different in the Tβ4 eye drops versus placebo treated eyes, with Tβ4-treated patients mitigating challenge effects.

TABLE 3

Ocular Discomfort Score Change during CAE - Change from visit 2 (baseline) visit 5

| Subpopulation | Ocular discomfort = 2, 3 | | Ocular discomfort = 0, 1 | |
|---|---|---|---|---|
| | Subject # | Change during CAE from baseline to visit 5 | Subject # | Change during CAE from baseline to visit 5 |
| Placebo | 90 | 0.50 | 14 | −0.86 |
| 0.05% | 83 | 0.23 | 19 | −0.05 |
| 0.1% | 84 | 0.06 | 18 | −0.61 |

Tear Amount

Increase in tear production was observed in the study. Schirmer's test results showed a change from a baseline of 0.26 in the placebo group, 0.88 in the 0.05% Tβ4-treated group and 0.67 in 0.1% Tβ4-treated group. This result indicated that the Tβ4 increased the tear amount in the dry eye patient. A low Schirmer's test result is indicative that the patient has small tear amount. Accordingly, a large positive change in Schirmer's test indicates an increase in tear amount and a negative change indicates a decrease of tear amount.

Moreover, in the higher corneal fluorescein staining group (i.e., the patients with a total corneal fluorescein staining score more than 5) at baseline, there was a distinction between the active and placebo treatment groups after the 28-day treatment (visit 5) with 0.05% and 0.1% Tβ4. When compared with baseline to visit 5, the Schirmer's test results were −1.00 in placebo group, 1.59 in the 0.05% Tβ4-treated group and 0.65 in 0.1% Tβ4-treated group (Table 4 below).

The lower corneal fluorescein staining group, however, (i.e., the patients with a corneal fluorescein staining score not more than 5) at baseline, the change of Schirmer's test results from baseline were 1.08 in placebo group, 0.45 in the 0.05% Tβ4-treated group and 0.65 in 0.1% Tβ4-treated group (Table 4 below).

This result indicated that the Tβ4 increased the tear amount in the severe dry eye patient group.

TABLE 4

Tear amount change from visit 2 (baseline) to visit 5 using Schirmer's test

| Subpopulation* | higher corneal fluorescein staining group | | lower corneal fluorescein staining group | |
|---|---|---|---|---|
| | Subject # | Change from baseline | Subject # | Change from baseline |
| Placebo | 43 | −1.00 | 60 | 1.08 |
| 0.05% | 39 | 1.59 | 64 | 0.45 |
| 0.1% | 48 | 0.65 | 54 | 0.65 |

Example 2: Safety and Efficacy of 0.05% and 0.1% Tβ4 Ophthalmic Composition in Combination with Artificial Tears Study Objectives The objective of this study is to compare the safety and efficacy of 0.05% Tβ4 ophthalmic composition in combination with artificial tears and 0.1% Tβ4 ophthalmic composition in combination with artificial tears to placebo for the treatment of the signs and symptoms of dry eye.

Materials and Methods

This study is a multicenter, randomized, double-masked study designed to evaluate the efficacy and safety of 0.05% and 0.1% Tβ4 ophthalmic solution in combination with artificial tears compared to placebo in subjects with dry eye.

Patients and Selection Criteria

Eligible patients are 18 years or older, have a reported history of dry eye for at least 6 months prior to enrollment, and have a history of eye drop use for dry eye symptoms within the previous 6 months.

The clinical dosage form and packaging of Tβ4 ophthalmic solution in combination with artificial tears and the placebo ophthalmic solutions are identical sterile, low-density polyethylene unit-dose non-preserved bottles. They are packaged in foil-wrap pouches to prevent light exposure, each containing single-use bottles. Throughout the study, between day 1 and day 29, patients are instructed to instill one drop of study medication in each eye four times daily, once in the morning, noon, afternoon and in the evening before bed. Patients are assigned randomization kit numbers in strict numerical sequence, using a code generated by an independent biostatistician. All investigators, study and site personnel, and patients are masked to the treatment assignments.

Results indicate that the Tβ4 in combination with artificial tears increase the tear film stability and reduce ocular surface damage of Tβ4-treated patients with a low tear film stability and the protective effect against adverse stimuli in the more severe symptomatic dry eye patients. Moreover, the treatment of Tβ4 in combination with artificial tears increases the tear amount in the severe dry eye patient group.

All patents, patent applications, publications, product descriptions and protocols, cited in this specification are hereby incorporated by reference in their entireties. In case of a conflict in terminology, the present disclosure controls.

While it will become apparent that the subject matter herein described is well calculated to achieve the benefits and advantages set forth above, the presently disclosed subject matter is not to be limited in scope by the specific embodiments described herein. It will be appreciated that the disclosed subject matter is susceptible to modification, variation and change without departing from the spirit thereof. Those skilled in the art will recognize, or be able to ascertain using no more than routine experimentation, many equivalents to the specific embodiments described herein. Such equivalents are intended to be encompassed by the following claims.

What is claimed is:

1. A method of reducing ocular surface damage in a subject in need thereof, comprising: delivering an ophthalmic composition containing from about 0.05% to about 0.1% by weight of an active agent, wherein the active agent is selected from the group consisting of Tβ4, a peptide comprising amino acid sequence LKKTET [SEQ ID NO:1], and a peptide comprising amino acid sequence LKKTNT [SEQ ID NO:2], wherein the subject has a tear film break up time of less than 10 seconds, wherein the subject has a lower tear film stability as compared to the subject having higher tear film stability, wherein the tear film stability is associated with dry eye syndrome, and wherein the subject has a mean change in inferior corneal fluorescein staining score that is less than half that of the subject having higher tear film stability after delivering the ophthalmic composition.

2. The method of claim 1, wherein the ophthalmic composition is formulated as a solution, suspension, semi-liquid, semi-solid gel, gel, ointment, or cream.

3. The method of claim 2, wherein the solution is administered to the subject in a form of eye drops.

4. The method of claim 1, wherein the method further comprises administering artificial tears to an affected eye of the subject.

5. The method of claim 4, wherein the artificial tears are administered simultaneously with the ophthalmic composition.

6. The method of claim 4, wherein the artificial tears and the ophthalmic composition are administered sequentially.

7. The method of claim 1, wherein the ophthalmic composition is administered to the subject at least once per day but no more than four times per day.

8. The method of claim 1, wherein the ophthalmic composition is administered to the subject once, twice, three, or four times per day.

* * * * *